US009248300B2

(12) United States Patent
Rys et al.

(10) Patent No.: US 9,248,300 B2
(45) Date of Patent: Feb. 2, 2016

(54) CONTROLLING WIRELESS COMMUNICATION IN AN IMPLANTED CARDIAC DEVICE

(75) Inventors: Kenneth D. Rys, Minneapolis, MN (US); Michael Andrew Reinert, St. Cloud, MN (US)

(73) Assignee: Medtronic, Inc., Minneapolis, MN (US)

(*) Notice: Subject to any disclaimer, the term of this patent is extended or adjusted under 35 U.S.C. 154(b) by 554 days.

(21) Appl. No.: 13/228,607

(22) Filed: Sep. 9, 2011

(65) Prior Publication Data
US 2013/0066169 A1  Mar. 14, 2013

(51) Int. Cl.
| | |
|---|---|
| A61B 5/02 | (2006.01) |
| A61N 1/372 | (2006.01) |
| A61B 5/024 | (2006.01) |
| A61B 5/07 | (2006.01) |
| A61B 5/11 | (2006.01) |
| H01Q 1/44 | (2006.01) |
| H01Q 9/27 | (2006.01) |
| A61B 5/00 | (2006.01) |

(52) U.S. Cl.
CPC ........ *A61N 1/37276* (2013.01); *A61B 5/02438* (2013.01); *A61B 5/076* (2013.01); *A61B 5/1107* (2013.01); *H01Q 1/44* (2013.01); *H01Q 9/27* (2013.01); *A61B 5/6869* (2013.01)

(58) Field of Classification Search
CPC ........ A61B 5/073; A61B 5/021; A61B 5/024; A61B 5/02438; A61B 5/026; A61B 5/028; A61B 5/0535; A61B 5/4362; A61B 5/04011; A61B 5/0452; A61B 5/0245; A61B 5/0464; A61B 5/222; A61B 5/0456; A61B 5/04004; A61B 5/044; A61B 5/0436; A61B 5/029; A61B 5/1102; A61B 7/04; A61B 5/0205; A61B 5/0215; A61N 1/3702

USPC .......................................................... 600/302
See application file for complete search history.

(56) References Cited

U.S. PATENT DOCUMENTS

| | | | |
|---|---|---|---|
| 6,427,088 B1 | 7/2002 | Bowman, IV et al. | |
| 6,507,759 B1 * | 1/2003 | Prutchi et al. | 607/60 |
| 6,585,644 B2 | 7/2003 | Lebel et al. | |

(Continued)

FOREIGN PATENT DOCUMENTS

WO    WO 2011/063848 A1    6/2011

OTHER PUBLICATIONS (PCT/US2012/053948) PCT Notification of Transmittal of the International Search Report and the Written Opinion of the International Searching Authority.

*Primary Examiner* — Patricia Mallari
*Assistant Examiner* — Vasuda Ramachandran
(74) *Attorney, Agent, or Firm* — Evans M. Mburu

(57) ABSTRACT

A relatively compact implantable cardiac medical device includes a wireless communications module, which employs a directional antenna and which is adapted to receive input concerning ventricular wall motion. When the cardiac medical device is anchored to a ventricular wall, transmitter elements of the communications modules are only activated for communication during a detected period of reduced ventricular wall motion. The period of reduced ventricular wall motion may be defined as at least one time interval during which an axis of the directional antenna does not rotate out from a baseline orientation by more than 15 degrees. The communication may be conducted with an external programmer-type device, or with another implanted device, for example, located remote from the heart.

29 Claims, 4 Drawing Sheets

(56) References Cited

U.S. PATENT DOCUMENTS

| | | |
|---|---|---|
| 6,659,948 B2 | 12/2003 | Lebel et al. |
| 6,811,534 B2 | 11/2004 | Bowman, IV et al. |
| 6,980,866 B2 * | 12/2005 | Yu et al. .................. 607/122 |
| 7,237,712 B2 | 7/2007 | DeRocco et al. |
| 7,338,436 B1 | 3/2008 | Snell et al. |
| 7,369,635 B2 | 5/2008 | Spital et al. |
| 7,650,186 B2 | 1/2010 | Hastings et al. |
| 7,904,167 B2 | 3/2011 | Klosterman et al. |
| 2002/0115939 A1 * | 8/2002 | Mulligan et al. ............ 600/510 |
| 2003/0163287 A1 * | 8/2003 | Vock et al. .................. 702/187 |
| 2005/0065445 A1 | 3/2005 | Arzbaecher et al. |
| 2007/0123786 A1 * | 5/2007 | Grandjean et al. ........... 600/509 |
| 2009/0048070 A1 * | 2/2009 | Vincent et al. .................. 482/8 |
| 2009/0082645 A1 | 3/2009 | Hafezi et al. |

\* cited by examiner

CONTROLLING WIRELESS COMMUNICATION IN AN IMPLANTED CARDIAC DEVICE

TECHNICAL FIELD

The present invention pertains to implantable cardiac devices and more particularly to systems employing the devices and methods for controlling wireless communications thereof.

BACKGROUND

The traditional implantable cardiac monitoring and/or therapy delivery system includes a medical device to which one or more flexible elongate lead wires are coupled. The device is typically implanted in a subcutaneous pocket, remote from the heart, and each of the one or more lead wires extends therefrom to a corresponding cardiac site, either endocardial or epicardial, in order to deliver therapy to, and/or monitor the site. Mechanical complications and/or MRI compatibility issues, which are sometimes associated with elongate lead wires and are well known to those skilled in the art, have motivated the development of relatively compact cardiac medical devices that can be implanted in close proximity to the cardiac site, for example, within the right ventricle (RV) of the heart, so that elongate lead wires are not required. With reference to FIG. 1, such a device 100 is illustrated, wherein a fixation member 115 anchors device 100 against the endocardial surface of the RV, for cardiac therapy delivery and/or monitoring, via medical components thereof, for example, a pair of electrodes, a mechanical transducer, and/or any other type of suitable sensor known in the art. Due to size constraints on device 100, limited space is available, within a hermetic enclosure/shell 101 thereof, for a power supply (i.e. battery) and circuitry (i.e. input/output circuit, a microcomputer circuit, memory, etc.) in support of the medical components. Device 100 is preferably accessible via wireless telemetry, for example, to update the programming of device 100 and/or to collect information from device 100, so a wireless communications module must also be contained within the limited space and supported by the contained power supply. In order to increase the life of the power supply, the most efficient operation of every component of device 100, including the communications module, is highly desirable.

SUMMARY

According to embodiments of the present invention, a relatively compact cardiac medical device includes a wireless communications module that employs a directional antenna; the communications module is adapted to receive input concerning ventricular wall motion in order to stabilize telemetry signal strength from the antenna and thereby make communication more efficient. According to methods of the present invention, when such a device is anchored to a ventricular wall, transmitter elements of the communications module are only activated for communication during a detected period of reduced ventricular wall motion. The period of reduced ventricular wall motion may be defined as at least one time interval during which an axis of maximum signal strength for the directional antenna does not rotate significantly out from a baseline orientation, for example, by more than approximately 15 degrees. Wireless communication, according to some embodiments, is conducted with an external programmer-type device, while, according to some alternate embodiments, the communication is conducted with another implanted device, for example, located at a site remote from the heart.

According to some embodiments, the cardiac medical device includes electrodes to detect the period of reduced ventricular wall motion, while according to alternate embodiments, the device includes a mechanical transducer to detect the period. According to yet further embodiments the device includes a pulse generator, and, when the device is implanted at an apical location of the right ventricle, pacing pulses are applied, according to some methods, in order to create the period of reduced ventricular wall motion.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
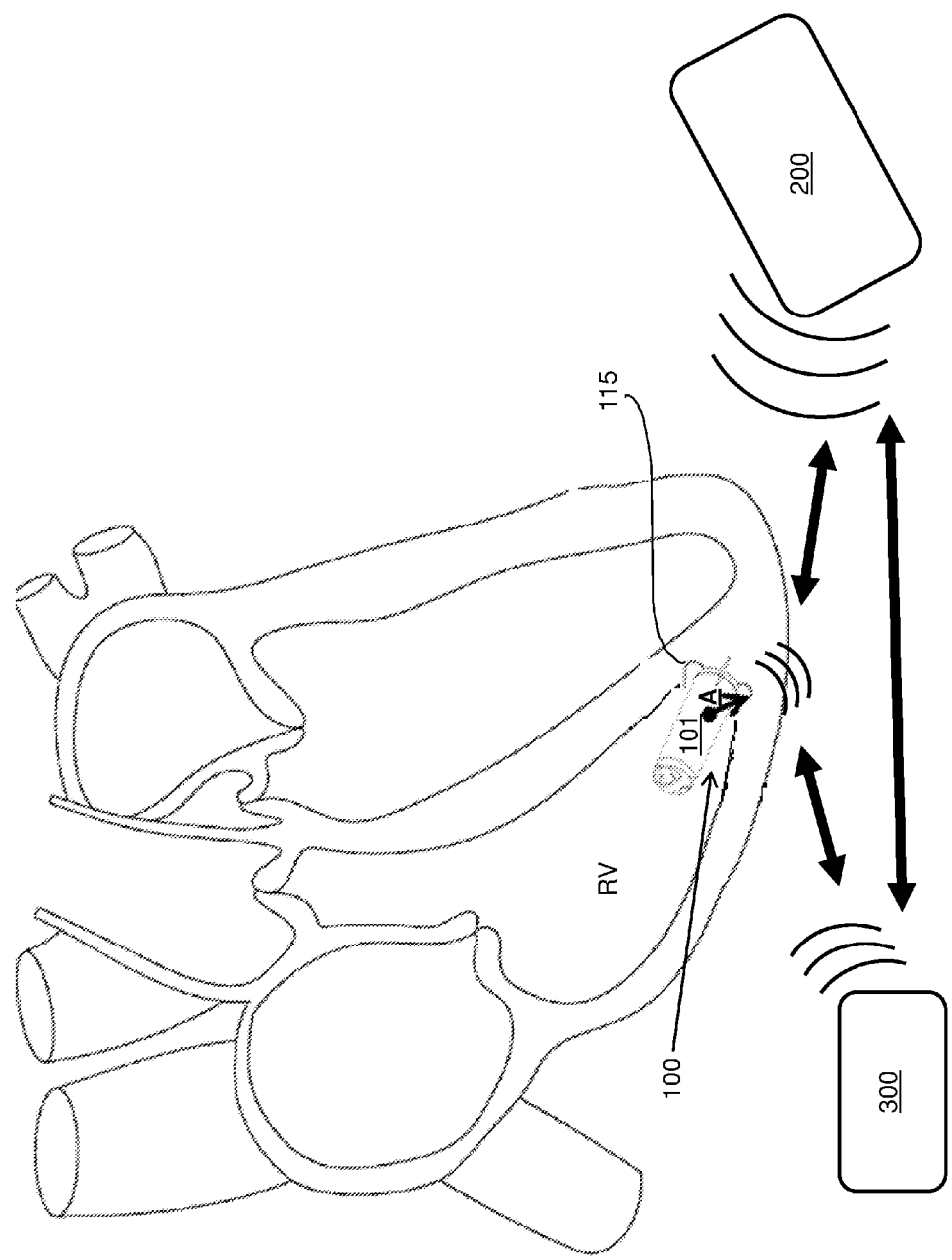
FIG. 1 is a schematic showing an exemplary cardiac medical device implanted in a right ventricle of a heart.
Figure 2A:
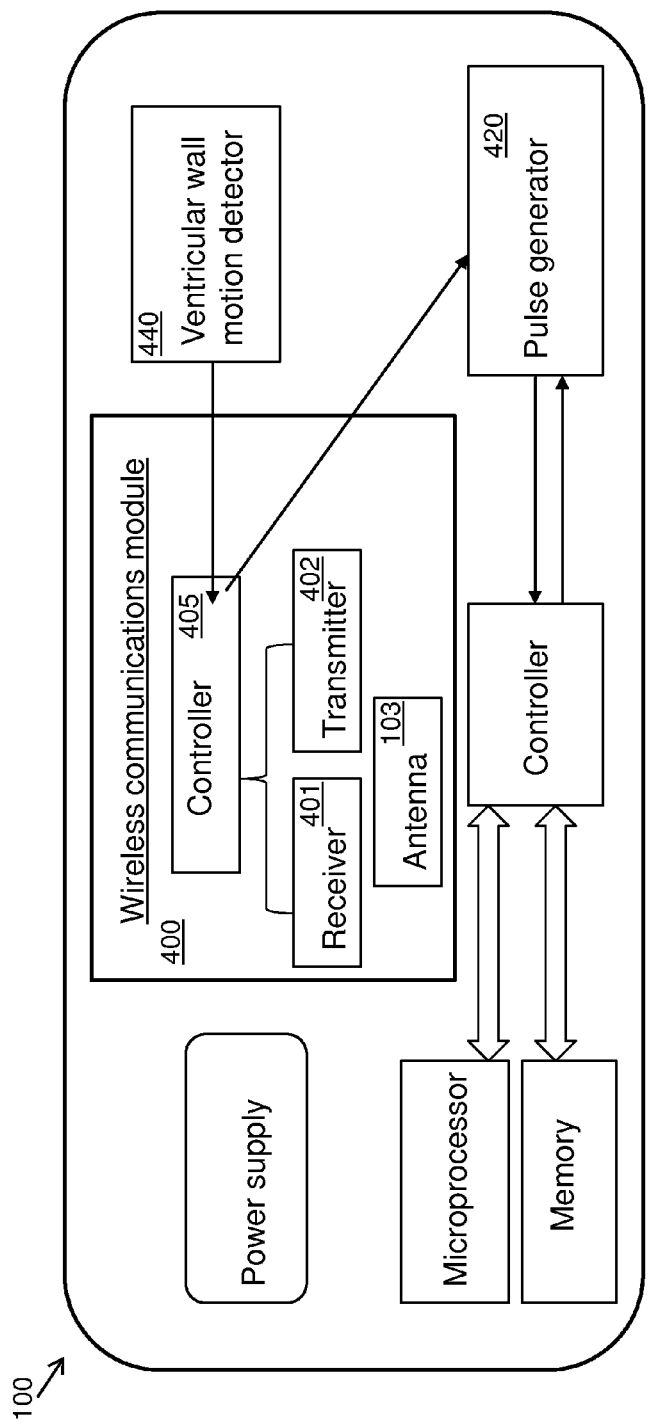
FIG. 2A is a block diagram showing main modules of an implantable cardiac medical device, according to some embodiments.
Figure 2B:
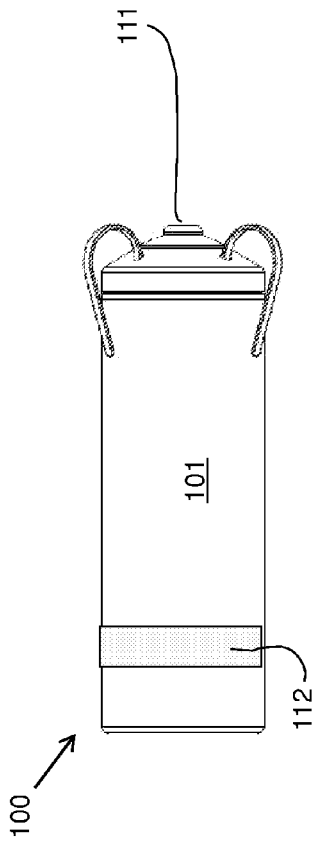
FIG. 2B is a plan view of the exemplary device of FIG. 1.

FIG. 1 illustrates device 100 with an axis A overlaid thereon to designate the direction of maximum signal strength from a directional antenna 103, which, with reference to FIGS. 2A-B is part of a wireless communications module 400 contained with shell 101 of device 100. At the time device 100 is implanted, radiopaque markers (not shown) included in device 100 may be viewed, via fluoroscopy, and/or telemetry signal strength, via antenna 103, may be monitored, in order to fix device 100 at the implant site in a particular orientation suitable to establish a favorable orientation of axis A. FIGS. 2A-B are a schematic block diagram and a plan view, respectively, for device 100, according to some embodiments. FIG. 1 further illustrates an external device 200, for example, an external programmer-type device, such as is known in the art, and another, optional, implanted device 300, either of which also includes a wireless communications module adapted for entering into wireless communications with device 100, according to any suitable configuration known in the art. According to preferred methods, a controller 405 of wireless communications module 400 of device 100 activates receiver elements 401 at predetermined/pre-programmed intervals to 'listen' for an activation signal from another device, such as device 200 or device 300, and once such a signal is detected, prepares for communication. If device 200 is a communication head of a programmer that requires positioning to align with axis A, for example, for inductive coupling telemetry, device 100 may transmit a beacon-type signal to help with the alignment of device 200. According to methods of the present invention, after controller 405 receives an activation signal from device 200, controller 405 activates transmitter elements 402 of communications module 400, but only according to input from a ventricular wall motion detector 440 of device 100.

Figure 3:
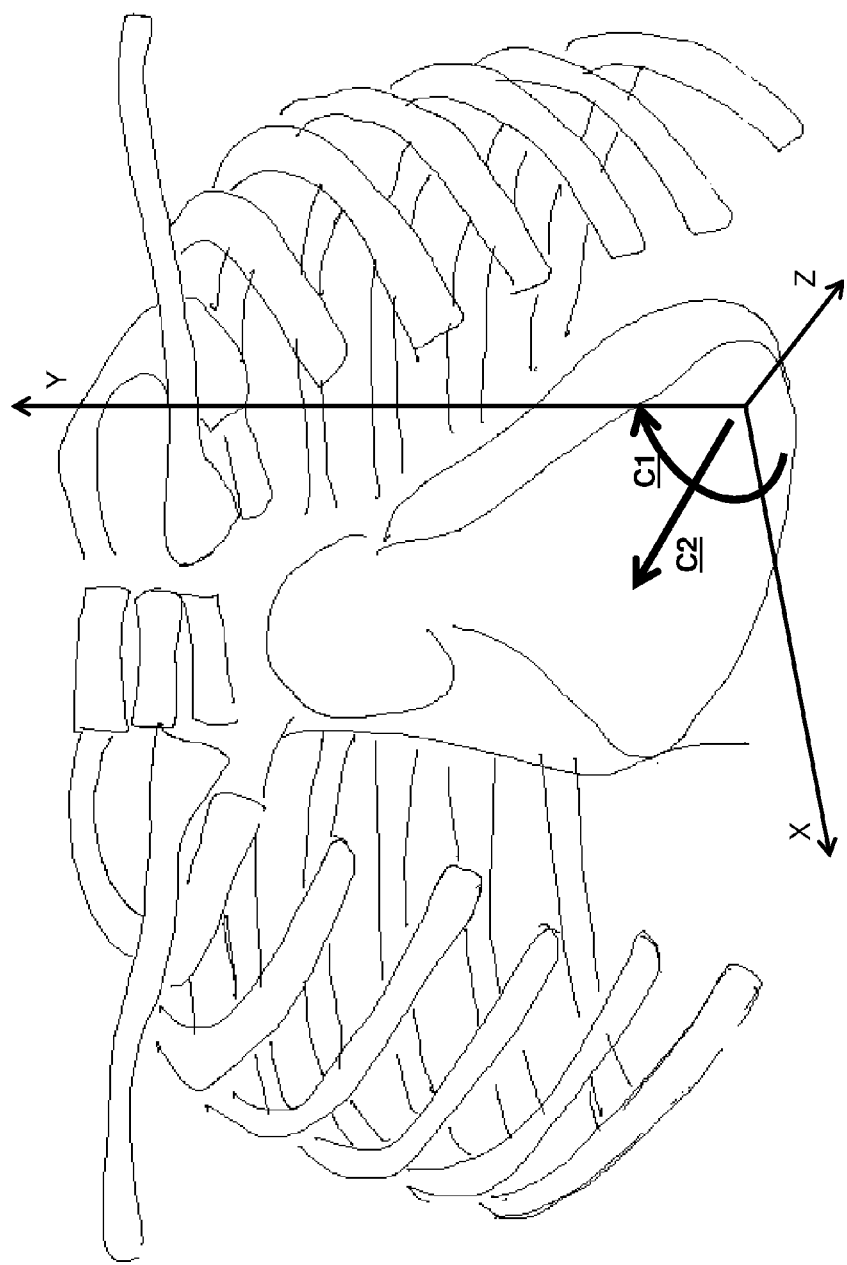
FIG. 3 is a heart wall motion schematic diagram.

With further reference to FIG. 2B, according to embodiments and methods of the present invention, ventricular wall motion detector 440 provides input to controller 450 of communications module 400, which, after the aforementioned activation signal is received from device 200, activates transmitter elements 402 only during a detected period of reduced ventricular wall motion. FIG. 3 is a schematic diagram showing orthogonal coordinate axes X,Y,Z overlaid on a heart in order to illustrate heart wall motion with each natural contraction of the heart. Those skilled in the art understand that the heart's intrinsic conduction system causes ventricular myocardium to contract with a twisting, or wringing (generally around axis Z), from the apex toward the base (generally along axis Z), per arrows C1 and C2, to squeeze blood out from the ventricles. With reference back to FIG. 1, since device 100 is anchored to the right ventricular wall, each natural ventricular contraction causes axis A to shift and rotate, so that an alignment of axis A with a corresponding axis of device 200 (as well as with that of device 300) changes during each contraction and causes a telemetry signal strength delivered via antenna 103 to sinusoidally alternate between approximately 0% and approximately 100%, thereby compromising wireless communication with device 100. According to some methods, the period of reduced ventricular wall motion includes one or more diastolic intervals between contractions (systolic intervals) of the heart. So, rather than powering up for transmission throughout the aforementioned sinusoidal variation caused by ventricular wall motion during systole, transmitter elements 402 are only powered during diastolic intervals, when the ventricular walls are relatively still for filling. During this period, a lower telemetry signal strength, which means less power consumption, is required from antenna 103, since the signal strength is relatively stable, thereby increasing the efficiency of outbound communication.

In addition to, or as an alternative to diastolic intervals, the period of reduced ventricular wall motion may be created by pacing stimulation, for example, delivered from a pulse generator 420 of device 100, when device 100 is implanted at an apical location, as illustrated in FIG. 1, at a rate that is greater (i.e. 10 to 20 beats per minute) than an intrinsic heart rate of the patient. Those skilled in the art understand that the ventricular wall motion, which corresponds to ventricular contractions that are externally stimulated from the apex of the heart, as opposed to those generated, from base to apex, by the heart's intrinsic conduction system, is reduced in the directions indicated by arrows C1 and C2 of FIG. 3. Thus pacing stimulation may extend the period of reduced ventricular wall motion into systolic intervals of each cardiac cycle. With reference back to FIGS. 2A-B, device 100 includes a pair of electrodes 111, 112, by which such pacing stimulation may be applied, wherein electrode 111 is coupled to internal pulse generator circuitry 420 via a hermetic feedthrough, known in the art, and electrode 112 is formed by an exposed conductive portion of shell 101, according to some embodiments. According to some methods, once an inbound activation signal is received, for example, from device 200 or device 300 (FIG. 1), by controller 405 of wireless communications module 400, via receiver elements 401, controller 405 sends a signal to activate pulse generator 420, in order to create the period of reduced ventricular wall motion via pacing stimulation. It should be noted that electrodes 111, 112 may also be employed by ventricular wall motion detector 440 for detection of the period of reduced ventricular wall motion that results from the applied pacing stimulation, as described below. The activation signal to create the period of reduced ventricular wall motion by the applied pacing stimulation is preferably sent by device 200 when the patient is in a clinical setting for a checkup, so that a clinician can monitor the patient's intrinsic heart rate, for example, to assure that the heart rate is a resting heart rate and stable before the higher rate pacing stimulation is applied. Furthermore, controller 406 of device 100 may have a programmable setting to limit the rate of applied pacing stimulation from the activated pulse generator 420, according to the patient's condition, for example, to prevent the stimulation from inadvertently triggering a cardiac arrhythmia.

According to some embodiments, ventricular wall motion detector 440 includes a mechanical transducer adapted to sense mechanical changes indicative of ventricular wall motion, for example, a pressure sensor for indirect detection of the period of reduced ventricular wall motion (i.e. intraventricular pressure changes over each cardiac cycle), an accelerometer for direct detection of reduced ventricular wall motion, a Doppler sensor to detect blood flow, or an auditory/acoustic sensor to detect heart valve, lung and/or blood flow sounds. According to alternate embodiments, ventricular wall motion detector 440 includes a pair of electrodes, for example, electrodes 111, 112 of FIG. 2B, which are adapted to sense electrical cardiac signals indicative of ventricular wall motion, for example, timing of the QRS complex to find diastolic intervals and/or QRS morphology to identify retrograde conduction resulting from applied pacing stimulation, for example, when the pulse generator is employed to create a period of reduced ventricular wall motion, as described above. According to yet further embodiments a chemical sensor may be employed in device 100, to provide additional input to controller 406, for example, of blood pH or blood oxygen saturation that may be indicative of a patient's physiological condition.

Figure 4:
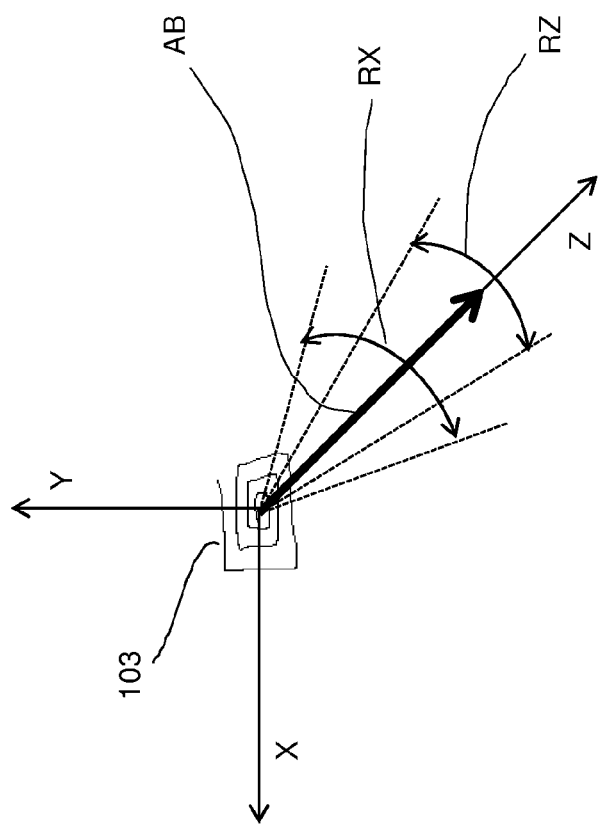
FIG. 4 is schematic diagram illustrating rotation of an antenna axis from a baseline orientation.

FIG. 4 is a schematic diagram illustrating a baseline orientation of axis A, designated AB, which corresponds to a best alignment of axis A with the maximum signal strength axis of the communications module antenna of another device, such as device 200 (FIG. 1). FIG. 4 further illustrates limits of rotation RX and RZ out from AB, about axes X and Z, respectively, within which the period of reduced ventricular wall motion is defined. According to some preferred embodiments, the limits of rotation RX and RZ are no greater than approximately 15 degrees, and rotation within these limits may be correlated to diastolic intervals and/or to extended intervals during pacing stimulation, as detected by ventricular wall motion detector 440. By means of in vivo experimentation that employed biplane fluoroscopic tracking of radiopaque markers attached to a device similar to device 100, which was implanted at an apical location (similar to FIG. 1), we have found that, when pacing stimulation was applied, device rotation during ventricular contractions, from a baseline orientation such as AB, is significantly reduced from that which was typical during intrinsic ventricular contractions.

With reference back to FIG. 1, according to some embodiments, third device 300 may be implanted at a site remote from the heart, for example, to monitor and/or deliver therapy. Communication between device 300 and device 100 may be necessary to coordinate therapy delivery, from one or both devices, and/or to transfer data/information from device 100 to device 300, for example, for storage in a data storage module of a memory of device 300 until predetermined time periods when an external device, such as device 200, is employed to retrieve the stored data/information. For example, device 300 may be a cardiac defibrillation generator that is implanted in an abdomen of the patient, a neuromodulation generator implanted in the abdomen or pectoral region, or a cardiac monitor implanted in the pectoral region, any of which, in addition to having a more stable axis of maximum wireless communication strength, by virtue of their implant location, may also have a size sufficient to include greater battery capacity and more sophisticated telemetry hardware (relative to device 100), for example, capable of long range and/or automated telemetry with an external device, which is known in the art.

In the foregoing detailed description, the invention has been described with reference to specific embodiments. However, it may be appreciated that various modifications and changes can be made without departing from the scope of the invention as set forth in the appended claims.

We claim:

1. A method for controlling wireless communication in an implanted cardiac medical device, the device being equipped with a wireless communications module, the device being anchored to a ventricular wall, and the method comprising:
   activating receiver elements of the communications module at predetermined intervals to receive an inbound activation signal;
   monitoring ventricular wall motion, wherein the ventricular wall motion includes a first ventricular wall motion period and a second ventricular wall motion period having a reduced rate of motion relative to the first ventricular wall motion period;
   detecting the presence of the second ventricular wall motion period; and
   activating transmitter elements of the communications module for outbound communication only after both:
   the inbound activation signal has been received and the second ventricular wall motion period has been detected.

2. The method of claim 1, wherein at least one time interval of the second ventricular wall motion period comprises a diastolic interval.

3. The method of claim 2, wherein the detecting results from sensing electrical cardiac signals.

4. The method of claim 2, wherein the detecting results from sensing mechanical cardiac signals.

5. The method of claim 1, wherein the device is anchored in an apical location, and further comprising applying pacing pulses from the device to create the second ventricular wall motion period.

6. The method of claim 5, wherein at least one time interval of the second ventricular wall motion period comprises a diastolic interval.

7. The method of claim 5, further comprising monitoring an intrinsic heart rate prior to applying the pacing pulses.

8. The method of claim 1, wherein the inbound activation signal is sent from an external device.

9. The method of claim 1, wherein the inbound activation signal is sent from another implanted device.

10. An implantable cardiac medical device configured to be wholly implanted at a cardiac site via anchoring to a ventricular wall, the device comprising a ventricular wall motion detector and a wireless communications module compatible for communication with another medical device; the communications module comprising receiver elements, transmitter elements and a controller, the controller adapted to receive input from the ventricular wall motion detector and being programmed to execute a method comprising the following steps:
   activating the receiver elements at predetermined intervals to receive an inbound activation signal from the other medical device;
   monitoring a signal from the ventricular wall motion detector for ventricular wall motion, wherein the ventricular wall motion includes a first ventricular wall motion period and a second ventricular wall motion period having a reduced rate of motion relative to the first ventricular wall motion period; and
   only after both the inbound activation signal has been received and the second ventricular wall motion period has been detected.

11. The device of claim 10, further comprising a pacing pulse generator, the pacing pulse generator being adapted to receive input from the controller of the wireless communications module; and wherein the method further comprises sending a signal to activate the pacing pulse generator, once the inbound activation signal is received and before activating the transmitter elements.

12. The device of claim 10, wherein at least one time interval of the second ventricular wall motion period comprises a diastolic interval.

13. The device of claim 12, wherein the ventricular wall motion detector comprises electrodes adapted to sense electrical cardiac signals; and the signal from the detector that indicates the presence of the second ventricular wall motion period results from sensing electrical cardiac signals.

14. The device of claim 12, wherein the ventricular wall motion detector comprises a mechanical transducer, the transducer being adapted to sense mechanical changes, either pressure or motion; and the signal from the detector that indicates the presence of the second ventricular wall motion period results from sensing mechanical changes.

15. A cardiac medical system comprising at least two devices, a first of the devices comprising a wireless communications module, and a second of the devices being configured to be wholly implanted at a cardiac site, via anchoring to a ventricular wall, and comprising a ventricular wall motion detector and a wireless communications module compatible for communication with the wireless communications module of the first device; the communications module of the second device comprising receiver elements, transmitter elements and a controller, the controller adapted to receive input from the ventricular wall motion detector and being programmed to execute a method comprising the following steps:
   activating the receiver elements at predetermined intervals to receive an inbound activation signal;
   monitoring a signal from the ventricular wall motion detector for ventricular wall motion, wherein the ventricular wall motion includes a first ventricular wall motion period and a second ventricular wall motion period having a reduced rate of motion relative to the first ventricular wall motion period; and
   activating the transmitter elements for outbound communication only after both the inbound activation signal has been received and the second ventricular wall motion period has been detected.

16. The system of claim 15, wherein the first device comprises an external programmer type device.

17. The system of claim 16, further comprising a third device configured to be implanted at a site remote from the heart; the third device being adapted for therapy delivery and/or data storage and including a wireless communications module compatible for communication with the communications modules of both the first and second devices; wherein the outbound communication from the second device is directed to the third device.

18. The system of claim 15, wherein the first device is configured to be implanted at a site remote from the heart; the first device being adapted for therapy delivery and/or data storage.

19. The system of claim 15, wherein the second device further comprises a pacing pulse generator, the pacing pulse generator being adapted to receive input from the controller of the wireless communications module of the second device; and wherein the method executed by the controller of the communications module of the second device further comprises sending a signal to activate the pacing pulse generator, once the inbound activation signal is received and before activating the transmitter elements.

20. The system of claim 19, wherein the controller of the wireless communications module of the second device includes a programmable setting to limit a rate of applied pacing stimulation from the activated pacing pulse generator.

21. The system of claim 15, wherein at least one time interval of the second ventricular wall motion period comprises a diastolic interval.

22. The system of claim 21, wherein the ventricular wall motion detector of the second device comprises electrodes adapted to sense electrical cardiac signals; and the monitored signal that indicates the presence of the second ventricular wall motion period results from sensing mechanical changes.

23. The system of claim 21, wherein the ventricular wall motion detector of the second device comprises a mechanical transducer, the transducer being adapted to sense mechanical changes, either pressure or motion, and the signal from the detector that indicates the presence of the second ventricular wall motion period results from sensing mechanical changes.

24. The method of claim 1, wherein the second ventricular wall motion period comprises at least one time interval during which an axis of a directional antenna of the communications module does not rotate out from a baseline orientation by more than approximately 15 degrees.

25. The device of claim 10, wherein the second ventricular wall motion period comprises at least one time interval during which an axis of a directional antenna of the communications module does not rotate out from a baseline orientation by more than approximately 15 degrees.

26. The system of claim 15, wherein the second ventricular wall motion period comprises at least one time interval during which an axis of a directional antenna of the communications module does not rotate out from a baseline orientation by more than approximately 15 degrees.

27. An implantable cardiac medical device configured to be anchored to a ventricular wall, the device comprising a ventricular wall motion detector and a wireless communications module compatible for communication with another medical device; the communications module comprising receiver elements, transmitter elements and a controller, the controller adapted to receive input from the ventricular wall motion detector and being programmed to execute a method comprising the following steps:
   activating the receiver elements at predetermined intervals to receive an inbound activation signal from the other medical device;
   monitoring from the ventricular wall motion detector a sinusoidal variation signal corresponding to motion of the ventricular wall;
   detecting a period of the sinusoidal variation signal corresponding to a diastolic interval; and
   activating the transmitter elements for outbound communication only after both the inbound activation signal has been received and the sinusoidal variation signal corresponding to the diastolic interval has been detected.

28. The device of claim 27, wherein the period of the sinusoidal variation signal corresponding to a diastolic interval comprises at least one time interval during which an axis of a directional antenna of the communications module does not rotate out from a baseline orientation by more than approximately 15 degrees.

29. The device of claim 27, wherein the sinusoidal variation signal includes a first segment corresponding to a first ventricular wall motion period and a second segment corresponding to a second ventricular wall motion period having a reduced rate of motion relative to the first ventricular wall motion period.

* * * * *